US006804902B1

(12) United States Patent
McCracken et al.

(10) Patent No.: US 6,804,902 B1
(45) Date of Patent: Oct. 19, 2004

(54) ADJUSTABLE ARCH SUPPORT ORTHOSIS INCLUDING VARIABLY TENSIONED ARCH CURVE AND METHOD OF UTILIZING ORTHOSIS

(76) Inventors: John C. McCracken, 5510 Ridgefield Dr., Knoxville, TN (US) 37912; W. Gilmer Reed, Jr., 509 Blount Professional Bldg., Knoxville, TN (US) 37920; Jack K. Greer, Jr., 116 Heritage Dr., Oak Ridge, TN (US) 37830

( * ) Notice: Subject to any disclaimer, the term of this patent is extended or adjusted under 35 U.S.C. 154(b) by 44 days.

(21) Appl. No.: 10/007,137

(22) Filed: Dec. 3, 2001

Related U.S. Application Data

(63) Continuation-in-part of application No. 09/723,063, filed on Nov. 27, 2000, now Pat. No. 6,393,736, which is a continuation-in-part of application No. 09/578,653, filed on May 25, 2000, now Pat. No. 6,345,455.

(51) Int. Cl.[7] .................................................. A61F 5/14
(52) U.S. Cl. .............................. 36/155; 36/145; 36/161; 36/91; 36/156
(58) Field of Search ..................... 36/91, 150, 155–162, 36/145, 166, 173, 147, 174, 180, 182, 88, 43–44; 12/146 M, 142 N; D2/961

(56) References Cited

U.S. PATENT DOCUMENTS

| 717,523 | A | | 1/1903 | Arrowsmith | |
| 1,136,443 | A | * | 4/1915 | Scholl | 36/155 |
| 1,657,367 | A | * | 1/1928 | Brownell | 36/155 |
| 2,157,454 | A | * | 5/1939 | Keys | 36/165 |
| 2,214,296 | A | * | 9/1940 | Early | 36/156 |
| 2,295,364 | A | * | 9/1942 | Skorepa | 36/156 |
| 3,794,037 | A | * | 2/1974 | Matteson | 36/156 |
| 4,166,329 | A | | 9/1979 | Herbig | |
| 4,571,857 | A | * | 2/1986 | Castellanos | 36/91 |
| 4,702,255 | A | * | 10/1987 | Schenkl | 36/145 |
| 4,813,157 | A | | 3/1989 | Boisvert et al. | |
| 5,400,528 | A | | 3/1995 | Skinner et al. | |
| 5,611,153 | A | | 3/1997 | Fisher et al. | |
| 5,903,985 | A | | 5/1999 | DeMarchi | |
| 6,345,455 | B1 | * | 2/2002 | Greer et al. | 36/155 |
| 6,393,736 | B1 | * | 5/2002 | Greer et al. | 36/155 |

* cited by examiner

Primary Examiner—Jila M. Mohandesi

(57) ABSTRACT

An arch support orthosis includes an arch curve being variably tensioned for supporting a user's arch and foot. The arch support orthosis includes a metatarsal curve, a curved heel portion and a continuous medial longitudinal arch curve. An anterior slope and posterior slope of the arch curve include varying thicknesses from the base of each slope to a crown of the arch curve. A greater base thickness of each anterior and posterior slope provides firm support of the respective anterior curve and posterior curve of a user's arch, with the crown being resiliently supportive of the user's arch during weighted and unweighted use. A means for tensioning having an adjusting means are connectable under the continuous arch curve between the anterior and posterior slopes, thereby allowing a user to adjust angles of the respective slopes and the tension along the arch curve for treating plantar fasciitis and other foot disorders.

4 Claims, 3 Drawing Sheets

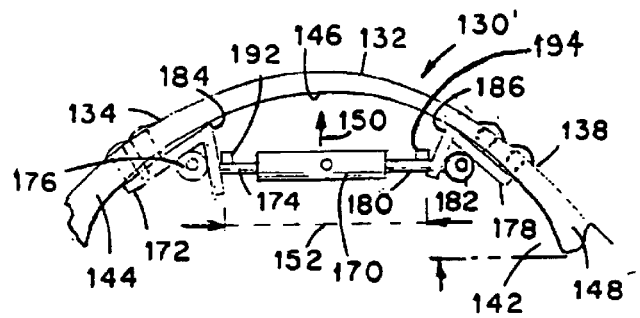
Fig. 4a
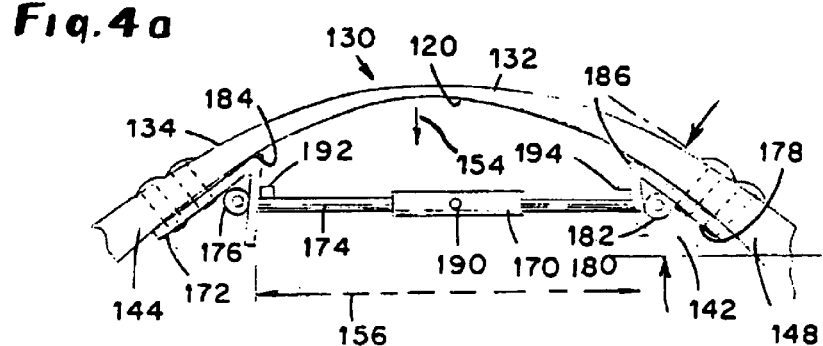
Fig. 4b
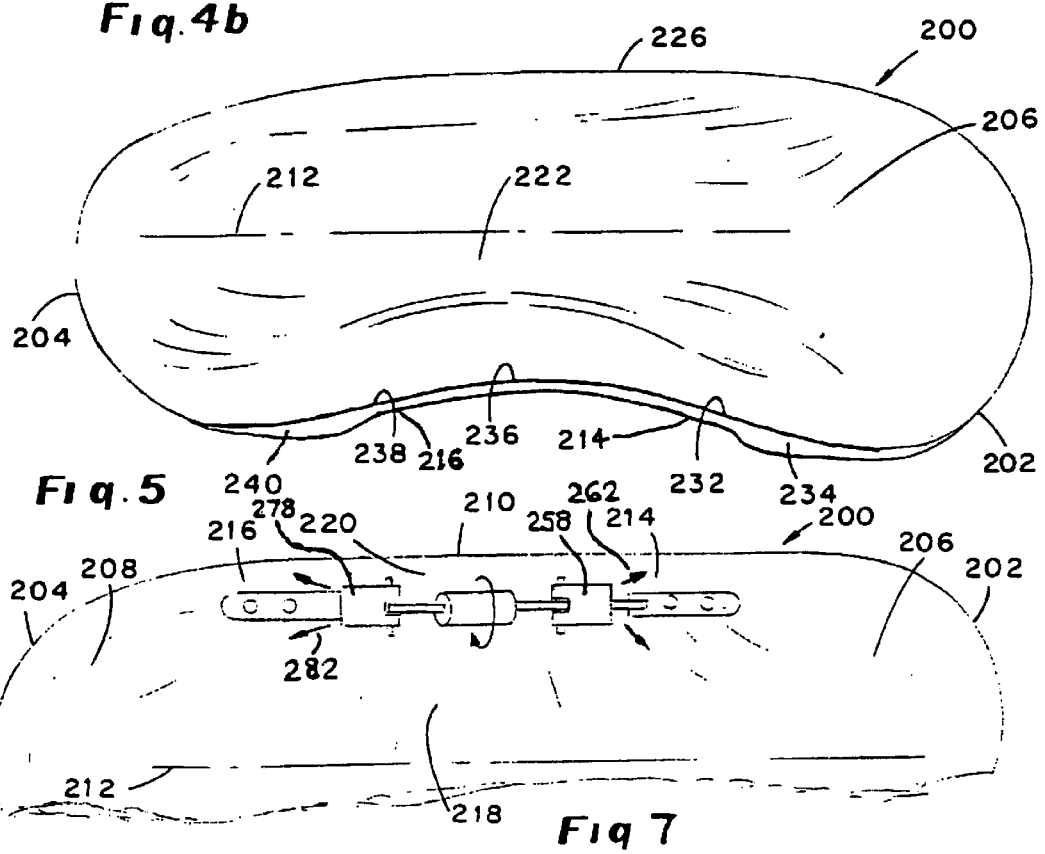
Fig. 5
Fig. 7

ADJUSTABLE ARCH SUPPORT ORTHOSIS INCLUDING VARIABLY TENSIONED ARCH CURVE AND METHOD OF UTILIZING ORTHOSIS

CROSS-REFERENCE TO RELATED APPLICATIONS

This application is a CIP of U.S. patent application No. 09723,063, filed on Nov. 27, 2000 now U.S. Pat. No. 6,393,736, entitled "Adjustable Arch Brace Orthotic And Method Of Treating Plantar Fasciitis And Related Foot Disorder", which is a CIP of U.S. patent application Ser. No. 09/578,653, filed on May 25, 2000 now Pat. No. 6,345,455, entitled "Orthotic Arc Support Including Self-Adjusting Arch Curve And Method of Using Orthotic."

STATEMENT REGARDING FEDERALLY SPONSORED RESEARCH OR DEVELOPMENT

Not Applicable.

BACKGROUND OF INVENTION

1. Field of Invention

This invention relates generally to the field of arch support orthosis for feet, and more particularly to a therapeutic arch orthosis including a variably tensioned arch curve and a method of utilizing the orthosis in treating foot disorders.

2. Description of Related Art

Prior foot support devices typically provide flexible cushioning material for support of an arch of a foot. Typical prior devices have provided pliable cushion pads that can be utilized to build up the cushioning materials for support of a heel or an arch. Other prior devices have provided shoes or boots that contain an integral and non-removable foot support structure that is installed as a single unit into a specially designed shoe or boot having an externally accessed adjustment screw or connector, which is not transferable to other shoes. The arch portions of prior pliable insoles were not adjustable without adding or removing layers of cushioning materials.

Prior foot instep supports typically provide an arch curve that is composed of flexible materials such as leather, foam, pliable plastic, and/or resilient sheet metal to provide comfort for the wearer of the foot instep supports. Prior insole or instep devices generally are made to have a similar thickness along the length of the insole, or have a solid arch portion composed of flexible rubber or compressible foam material having a thickness extending continuously from the arch surface to a generally flat base of the insole. The prior foot instep supports were malleable and did not retain a rigid shape. The prior foot instep supports were purposefully made of malleable and flexible materials to allow changing of the curvatures to fit a user, and/or to allow the instep supports to be bent to fit into different styles of shoes. The heel and/or arch curve portions of prior instep supports were typically compressed over periods of extended use, with little or no repetitive rebound properties for retention of the original curvature of the arch portion or the instep support portion. With no retention of the original curvature of the arch portion of prior instep supports, the arch portion would fail and flatten with use, and a user's arch curve was not properly supported after extended use of prior instep supports, leading to arch pain and/or heel pain identified in layman's terms as "falling arches."

The prior arch support devices only provided arch adjustments that require replacements of stackable members of cushioning. Other foot support devices require lateral movement of arch support portions controlled by adjusting connectors external to the shoe, and which require significant shoe modifications to permanently install within enclosing shoes or sports boots. The stackable members of cushioning deformed and flattened during extended use, and the foot support devices permanently installed within shoes were not transferable to other pairs of shoes.

Medically dispensed shoe orthotics typically provide a rigid orthotic having been generated from a cast formed of a patient's foot. The medically dispensed orthotic typically extends a partial length of the foot, from the toes to the arch portion, of from the arch portion to the heel portion, or extends the full length of the foot. The medically dispensed orthotic is not adjustable in overall length or in arch curve height, therefore when a user's foot changes due to growth, or an arch curve resumes a pre-injury height, the cast-formed orthotic is discarded and an additional cast formed orthotic is required to be generated by a medically trained professional to adequately support the foot.

Commercially available sport shoe inserts typically provide a cushioned cover over a rigid length of plastic. The rigid length of plastic may extend from the arch curve portion to a heel portion of the foot, or may extend from the toes to the heel portion of the foot. The sport shoe insert typically is available in one or two arch curve heights such as a "high arch" or "medium arch" style, with the same arch curve height provided for both of the right and left shoe inserts. The user is expected to select a foot length and arch curve height (high or medium arch), that matches his or her foot, and the user is typically not provided with assistance from a trained professional. A user having a "low arch" must utilize a "medium arch" style, or locate a lower arch support insert.

There is a need for an adjustable arch support orthosis providing therapeutic rigid support of the longitudinal arch of the feet, with the orthosis transferable between pairs of footwear. A need exists for an adjustable arch support orthosis including a generally rigid medial longitudinal arch curve that is variably adjustable in tension along the slope of the arch curve during each weighted and unweighted cycle of walking and running. A further need exists for an adjustable arch curve orthosis including a generally rigid medial longitudinal arch curve having a means for adjusting the tension along the arch curve, to allow a user to adjust the tension and height of the arch curve for proper fit under each arch of the right and left foot, and for proper fit in various styles of footwear.

An additional need includes providing a method for utilizing an arch support orthosis being adjustable in tension along the arch curve, including varying the tension along the arch curve of the arch support orthosis for treatment of foot disorders under the supervision of a medical professional for a user suffering from heel spurs, plantar fasciitis, arch pain, tendinitis, metatarsalgia, and related foot disorders. A need exists for a method of adjusting the tension along the arch curve of an adjustable arch support orthosis, with maintenance over repetitive uses of a preferred arch curve tension and slope for support of the user's arches of the feet, with minimal training of the user and without the need for daily or weekly supervision of a medical professional.

BRIEF SUMMARY OF INVENTION

The invention comprises an arch support orthosis including an adjustable arch curve being variably tensioned and being continuous along the arch curve surface. The arch support orthosis is positionable underneath the foot and is sized and shaped to be removably placed in a shoe or other foot enclosure worn by a user. The arch support orthosis includes a plurality of contoured surface curves for support of the plurality of contours across the width and along the length of the underside of the foot. The arch support orthosis includes a metatarsal curve to support the metatarsal bones of the forefoot portion, includes a curved heel portion to support the calcaneus bone of the heel portion, and includes an interior upwardly arched side and an outer curved lateral edge. A continuous arch support curve (hereinafter, arch curve) of the orthosis includes a medial longitudinal arch surface along the interior upwardly arched side. The arch curve includes an anterior slope that is inclined at an anterior angle to form the leading portion of the arch curve. The arch curve includes a posterior slope that is inclined at a posterior angle to form the trailing portion of the arch curve. The arch curve further includes a medial slope that is inclined from a crown of an upper surface of the medial longitudinal arch surface towards the outer lateral edge of the orthosis. The anterior slope add the posterior slope includes a varying thickness having a depth and thickness of material that varies from the base of each slope to the upper portion of each slope along a crown of the arch curve. The base thickness of each slope is generally thicker than the thickness of the upper portion of each slope. The crown of the arch curve includes a lesser thickness than the base thickness of each slope to provide a variable thickness arch curve that is pliable and resilient along the crown for support of the mid-portion of a person's arch. The greater base thickness of each anterior and posterior slopes provides firm support of each respective anterior curve and posterior curve of a person's arch, while minimizing the degeneration of the rigidity of the arch curve over prolonged utilization in support of each respective arch. The respective base portions of each slope and the crown portion of the arch curve are respectively rigid along the base and the mid-portion of each slope, while being resilient along the crown for appropriate support of each respective portion of the user's arches during utilization of the adjustable arch support orthosis.

A means of tensioning is connectable under the continuous arch curve, and includes an adjusting means attached thereon. The tensioning means and adjusting means allows the user to adjust the anterior angle of the anterior slope, the posterior angle of the posterior slope, and to adjust the tension along the slopes and the crown of the arch curve. The variably tensioned arch curve provides a user with multiple adjustments of the tension and height parameters of the arch curve for therapeutic treatment of various foot conditions. The arch support orthosis is easily removable without readjusting the tension and height parameters of the arch curve for placement in any pair of footwear.

The present invention further discloses a method of utilizing the arch support orthosis for treatment of inflamation and pain in the foot by applying an arch support orthosis having a variably tensioned continuous arch curve under the foot. The method includes selectively and periodically adjusting the tension along the arch curve, and the angle of the anterior and posterior slopes of the arch curve, by the wearer's manipulating of the tensioning and adjusting means attached under the arch curve. The method provides therapeutic support and strengthening of the wearer's arches to relieve inflamation and pain associated with plantar fasciitis and/or tendinitis of related connective tissues and joints of wearer's foot.

BRIEF DESCRIPTION OF SEVERAL VIEWS OF THE DRAWINGS

The above mentioned features of the invention will become more clearly understood from the following detailed description of the invention contained herein, read together with the drawings in which:

FIG. 4a is a partial side view of FIG. 2, illustrating an embodiment of the means for tensioning positioned in a first tensioned configuration for support of a high arch of a user's right foot;

FIG. 4b is a partial side view of FIG. 2, illustrating the means for tensioning positioned under the medial longitudinal arch curve in a second tensioned configuration for support of a medium arch of a user's right foot;

FIG. 5 is a perspective top view illustrating an alternative embodiment of an arch support orthosis including a tensioned arch curve having generally rigid base supports for each anterior and posterior slopes of the medial longitudinal arch curve;

FIG. 7 is a partial bottom view of FIG. 6, illustrating the medial longitudinal arch curve having attached underneath an alternative embodiment of a means for tensioning for variably tensioning the medial longitudinal arch curve;

DETAILED DESCRIPTION OF THE INVENTION

Figure 1:
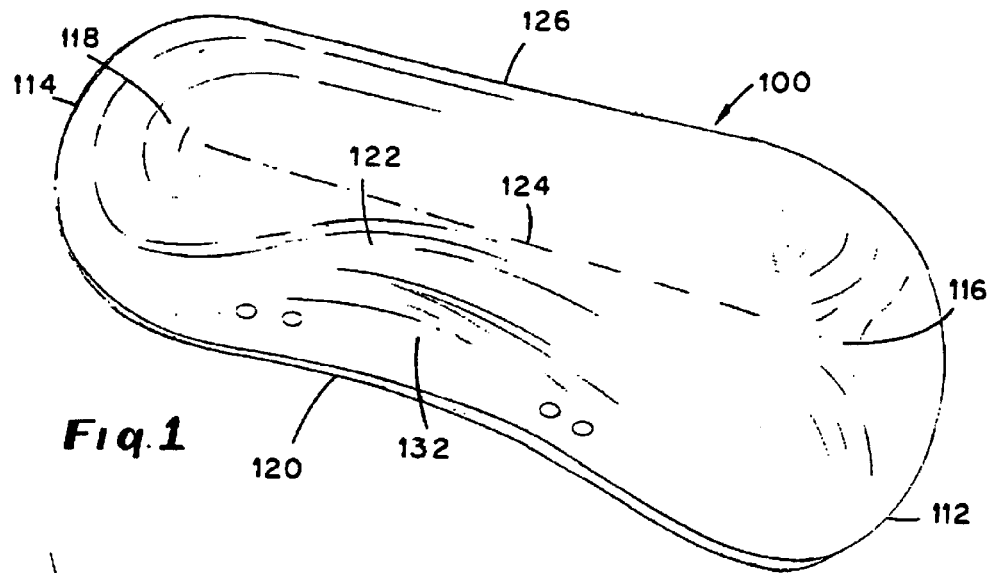
FIG. 1 is a perspective top view of an arch support orthosis including a variably tensioned arch curve of the present invention.
Figure 6:
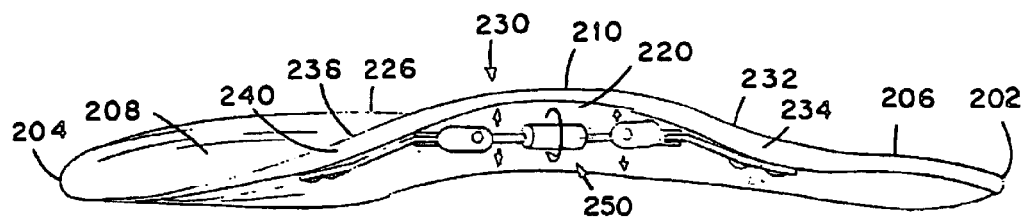
FIG. 6 is a side view of FIG. 5, illustrating an interior side of a medial longitudinal arch curve including an alternative embodiment of a means for tensioning for variably tensioning the arch curve of an arch support orthosis of the present invention.

An adjustable arch support orthosis and method of adjusting the arch curve thereof is disclosed incorporating various features of the present invention as illustrated generally for an adjustable arch support orthosis at 100 in FIG. 1, at 200 in FIG. 5, and at 210 in FIG. 6. The arch support orthosis includes a contoured orthotic platform sized to support the foot of a user from approximately the forefoot 112 end, to about the heel end 114 of the foot 198 of a user (see FIG. 1 and 2). The forefoot 112 region includes a transverse arch curvature 116 for support of the metatarsal bones of the forefoot (see FIG. 1 and 2). The posterior 114 region includes a concave heel section 118 for support of the calcaneus heel bone of the talus area of the foot 198 (see FIGS. 1–3).

Each of the arch support orthosis 100, 110, 200, 210 can be sized and shaped in various lengths and widths, and each include adjustable arch tensioning and arch height control to accommodate users having a narrow, rigid foot with a high arch (pes cavus), a medium arch, or can be sized and shaped to accommodate users having a generally more flattened foot (pes planus). Each respective arch support orthosis is sized for support of either the left foot or right foot of a user. Each arch support orthosis 100, 110, 200, 210 is removably positioned underneath the foot of a user in any of the owner's shoes, and is positioned upon a foot supporting surface within the shoe such as on or under the insole of any appropriately sized shoe or sandal. The arch support orthosis is shaped and proportioned to replace the insole of a foot support enclosure. The arch support orthosis is contoured for support of the arch of a right foot or a left foot, and is utilizable together as a pair of right and left arch support orthoses for simultaneous treatment of inflamation and pain in both user's feet. The arch support orthosis is quickly removable and repositioned by the user in any type of footwear such as athletic shoes, walking shoes, dress shoes, casual shoes or sandals, ski boots, and/or work boots, without disassembly of the arch support orthosis and without changing the tension of the arch curve portion of the adjustable arch support orthosis 100, 110, 200, 210.

One embodiment of the arch support orthosis 100 includes an interior arched side 120 of an upwardly arched, continuous, medial longitudinal arch curve 130 (hereinafter, arch curve) which includes an upper, non-segmented portion referred to as an upper crown surface 132, and a central mid-portion arch slope 122 having a sloped portion extending toward a lengthwise center midline 124. The arch curve 130 slopes downwards in a forward direction towards the transverse arch curvature 116, and slopes downwards in a rearward direction towards the concave heel section 118. The arch curve 130 also slopes laterally outwards towards an outer edge 126 (see FIG. 1). The lengthwise center midline 124 extends from about the transverse arch curvature 116 to the concave heel section 118. On the outer side of the lengthwise central midline 124 is the outer edge 126 that is sloped slightly upwards along the outer perimeter of the arch support orthosis for support of the outer lateral portion of the foot 198. The underside 12 of the forefoot portion 112 and heel portion 114 of the orthosis 100 is generally curved in proportion to the upper surfaces of the orthosis.

Figure 2:
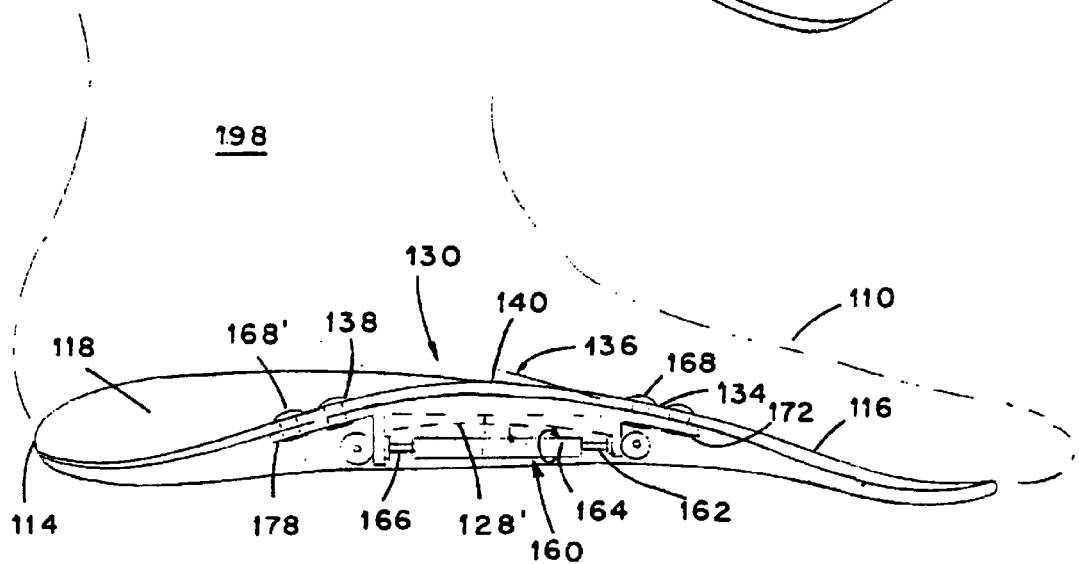
FIG. 2 is a side view of FIG. 1, illustrating an interior side of a medial longitudinal arch curve for support of an arch of a user's left foot, illustrating a means for tensioning positioned under the medial longitudinal arch curve.
Figure 3:
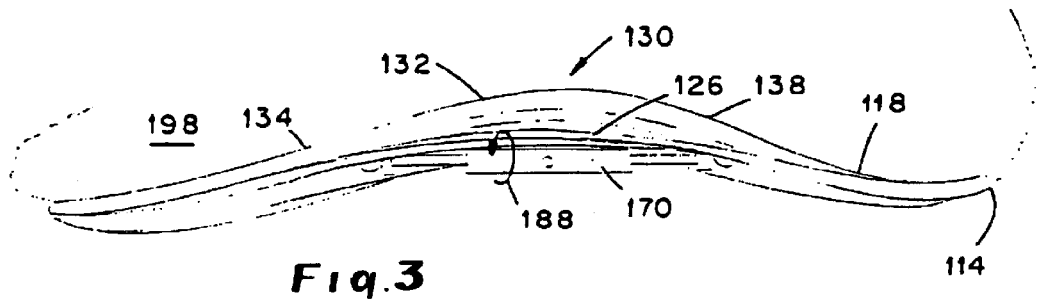
FIG. 3 is an opposed side view of FIG. 2, illustrating the plurality of curved surfaces of the medial longitudinal arch curve for support of a user's left foot.

As illustrated in FIGS. 1–3, one embodiment of the arch support orthosis 100 provides a thickness of the interior arched side 120 of the arch curve 130, and a thickness of portions of the anterior arch slope 134, crown 132, and the posterior arch slope 138, that are generally similar thicknesses to provide an even distribution of tension along the arch support curve 130. The arch curve 130 illustrated in FIGS. 1–3 includes a continuous, non-segmented arch curve 130 including an anterior arch slope 134 having an anterior slope angle 136, and including a posterior arch slope 138 having a posterior slope angle 140 (see FIG. 2). The descending posterior slope angle 140 includes an angle of declination 142 (see FIG. 4a and 4b) in a range of between about 12 degrees angle to about 20 degrees angle. The angle of declination 142 is preferably maintained within a range of about 14 degrees angle to about 16 degrees angle for adequate support of the posterior portion of the curved arch of a user's foot 198. For therapeutic support of the arch of a user's foot, and for treatment of many foot disorders, it is important to maintain the angle of declination within, or close to, the preferred range of angles for therapeutic support of the user's arch along the posterior arch portion proximal to where the plantar fascia is connected to the calcaneus bone of the user's foot 198.

In order to adjust the tension along the arch curve 130, 130' and to maintain the angle of declination 142 within a preferred range of angles, a means for tensioning 160, 170 is releasably attachable between an anterior bracket 172, and a posterior bracket 178, connected under each surface of the respective anterior arch slope 134 and the posterior arch slope 138. The means for tensioning 160, 170 may include any rotatable 188 or similarly manipulated adjustment means 164, 170 known to those skilled in the art for adjusting the length between two opposed ends connected to the anterior bracket 172 and the posterior bracket 178. Examples of one embodiment of the means for tensioning 160 includes an anterior cable or rod 162 and a posterior cable or rod 166 that are generally rigid in a length dimension, but may be somewhat flexible in a lateral direction. A rotatable means 164 for adjusting the length between the anterior and posterior cable ends includes adjusting devices such as a sleeve nut, worm gear, or a small-sized turnbuckle (not shown). When the user manipulates the means for adjusting 164, either by finger manipulation or by use of a small-sized tool, the anterior cable 162 and posterior cable 166 are retracted in overall length between the cable ends, thereby pulling each respective anterior bracket 172 and posterior bracket 178 toward the means for adjusting 164 with a shortening 152 of the tensioning means 160 (see FIG. 2 and 4a). As tension is placed on each respective anterior bracket 172 and posterior bracket 178 by the shortened tensioning means 160, the bracket connectors 168, 168' draw each respective connected portion of the anterior arch slope 134 and posterior arch slope 138 together, thereby inducing additional tension along the arch curve 130, forming a more rigid arch curve 130, and slightly increasing the height of the arch curve 130, providing firm and generally rigid support of a user's arch. When the means for adjusting is manipulated in a direction to lengthen the tensioning means 160, the length between the ends of anterior cable or rod 162 and posterior cable or rod 166 is extended due to the push of anterior end 176 against one portion of anterior bracket 172, and extension of tab 192 against a downwards projection of bracket 172, forcing pivoting at an anterior pivot 184 Posterior cable or rod 166 is extended to push against posterior bracket 178 by the push of posterior end 182 against one portion of bracket 178, and extension of tab 194 against a downwardly projection of bracket 178, forcing pivoting at a posterior pivot 186. Extension of the ends of anterior cable 162 and posterior cable 166, with resulting reduction of the tension along the arch curve, and a slight decrease in the height of the arch curve to a neutral height, while retaining a neutral tension along the arch curve 130.

An alternative embodiment of the arch support orthosis 110 includes an arch support curve 130' having a tensioning means 170 and a rotatable means for adjusting 190 attached underneath as illustrated in FIGS. 4a and 4b. A variable thickness along the arch support curve 130' is disclosed for portions of the anterior slope 134 and posterior slope 138 of the arch curve 130'. For the underside 128' portion of the arch curve 130', an anterior base portion 144 and a posterior base portion 148 are increased in thickness in a range of about 3 mm and greater, than a comparably thin thickness 146 of the upper crown 132 portion having a range of about 1 mm to about 3 mm. A rigid arch curve 130' is provided to support heavily weighted users, and/or athletically inclined users, with the thicker base portions 144, 148 being configured to diminish flex along the anterior slope 134 and posterior slope 138 during adjustable tensioning of the arch curve 130' by a user manipulating of a means for tensioning 170. With diminished flex of the arch curve 130' by lateral and downward forces placed against the upper crown surface 132, as during repetitive forceful foot-strikes during walking, running, and other athletic activities, a failure indicative of flattening of the previous arch supports is diminished by a rigid arch curve 130' having the means for tensioning 170 connected underneath according to observations during testing with a variety of users of various weights and arch heights while wearing the adjustable arch support orthosis 100, 110 of the present invention.

During tensioning of the arch curve 130' by manipulating and shortening 152 (see FIG. 4*a*) of the means for tensioning 170, an increased tension is created along the arch curve 130' with limited raising 150 of the height of the arch curve 130'. When the means for tensioning 170 is lengthened in length 156 (see FIG. 4*b*), a decreased tension is created along the arch curve 130' with limited lowering 154 of the height of the arch curve 130'. A generally resilient upper crown portion 132 is formed by having a comparably thin thickness 146 of the crown portion 132, while maximizing the rigidity of the base of the arch curve 130' by including increased thickness of the anterior slope base portion 144 and the posterior slope base portion 148 (see FIGS. 4*a* and 4*b*).

As illustrated in FIG. 5, an alternative embodiment of an arch support orthosis includes a foot support platform 200 having a plurality of curved surface portions including a forefoot support end 202, a heel support end 204, a metatarsal arch portion 206, a concave heel cup 208, an upwardly arched and continuous medial side 212, and an outer lateral side 226 contoured upwards at the outer edge of the foot support platform 200. The arched medial side 212 is generally aligned along the interior length of the foot support platform 200 and includes an arch curve 230 arched above the foot support platform 200. The arch curve 230 includes an anterior arch slope 232, an anterior slope base 234 having an increased thickness compared to the upper portion of the anterior arch slope 232, a posterior arch slope 238, a posterior slope base 240 having an increased thickness compared to the upper portion of the posterior arch slope 238, and a central slope 242 that extends to about the midline 222 of the orthosis. The central slope 242 may extend past the midline 222 for embodiments designed to support a high arched user. A crown portion 236 forms the crest of the arch curve 230, and may have a thickness of about 1 mm to about 3 mm. The thickness of the upper portion of the anterior arch slope 232, the upper portion of the central slope 242, and the upper portion of the posterior arch slope 238, may be in the range of about 2 mm to about 4 mm in thickness, with the thickness of the anterior and posterior arch slope increasing toward the base portions 234, 240. The thickness of the lower portion of the central slope 242, proximal to the midline 222, may be in the range of about 2 mm to about 4 mm, and greater in thickness. The range of the thickness of the forefoot 202, heel 204, and outer side 226 portions of the orthosis 200, may be in the range of about 2 mm to about 4 mm, independent of the variable thickness of respective portions of the arch curve 250. The orthoses 100 110, 200, 210 may be composed of generally rigid materials known to those skilled in the art, including high-density polymer materials such as Delrin® by Dupont, graphite composite materials, ceramic materials, aluminum, copper, steel or another generally rigid material. When the orthoses 100, 110, 200, 210 are composed of aluminum, copper, steel or another metal material, the thicknesses of each portion of the orthosis, including the arch curve portion, may be decreased by about a 1 mm increment while providing substantially rigid support of the user's arch and foot.

As illustrated in FIGS. 6, 7, 8*a* and 8*b*, an alternative orthosis includes a foot support platform 210 having an underside 218 of the arch curve 230, to which a tensioning means 250 is attachable. The foot support platform 210 includes a generally aligned and continuous arched medial side 212, an underside 220 configured to have an underside anterior slope portion 214 and a posterior slope portion 216 to which connecting brackets are connectable for attachment therebetween of the tensioning means 250. The thickness and depth of anterior slope base 234 allows for connectors 268 to be connected into the anterior slope base 234, which may have a thickness of about 3 mm and greater in thickness. The thickness and depth of posterior slope base 240 allow for connectors 288 to be connected into the posterior slope base 240, which may have a thickness of about 3 mm and greater in thickness. The thickness of the anterior slope base 234 may be less than, or greater than, the thickness of the posterior slope base 240, depending on the rigidity required for the anterior portion compared to the posterior portion of the arch curve 230, to support the user's arch during extended use of the orthosis 200, 210.

Figure 8A:
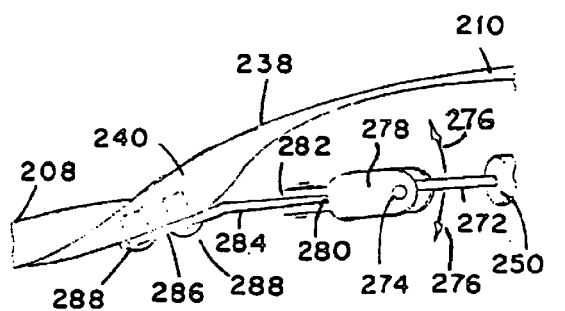
FIG. 8a is a partial side view of FIG. 6, illustrating the posterior slope of the medial longitudinal arch curve having a means for tensioning for variably tensioning the arch curve of the present invention in support of a user's left arch and foot.
Figure 8B:
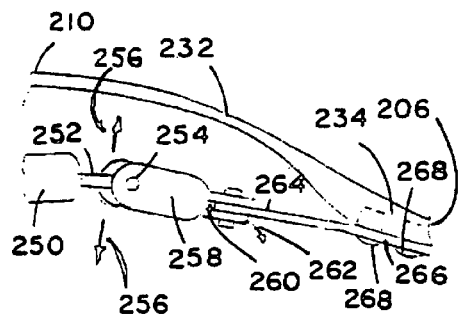
FIG. 8b is a partial side view of FIG. 6, illustrating the anterior slope of the medial longitudinal arch curve having a means for tensioning for variably tensioning the arch curve of the present invention in support of the user's left arch and foot.

As illustrated in FIGS. 6, 7, 8*a* and 8*b*, the foot support platform 210 includes a means for tensioning 250 having connector brackets attachable along the S underside anterior slope portion 214 of the anterior slope base 234, and along the posterior slope portion 216 of the posterior base 240. As illustrated in FIGS. 6 and 7, the means for tensioning 250 includes a plurality of movement for pivoting 256,276 in a vertical direction, and for swiveling 262, 282 in a lateral direction for the connections of the means for tensioning in relationship with the connector brackets 264, 284. As illustrated in FIG. 8*b*, an alternative means for tensioning 250 includes a generally rigid anterior member 252 such as a rod or cable connected to an anterior end of a means for adjusting 270 that is adjustable by a user to length or shorten the extended end of the member 252. An anterior connector 254 is connected through a slotted connection within an anterior joint member 258 to an anterior end of the member 252, to allow pivoting 256 in an up and down, generally vertical, direction of the anterior end of the member 252. The anterior joint member 258 includes an anterior slot 260 into which a second end 264 of a connector bracket 266 is insertable. The anterior slot 260 of joint member 258 is attachable with bracket portion 264 to allow for lateral motion 262 (see FIG. 7) of the anterior end of 258. Bracket portion 264 is integral with anterior bracket portion 266 which is connected with connectors 268 such as rivets or screws to the anterior slope base 234. The bracket portion 264 and anterior bracket portion 266 may include an angle therebetween to provide the necessary alignment with anterior slot 260 and the underside anterior slope portion 214 of the anterior slope base 234. The thick anterior slope base 234 provides rigidity for the anterior slope 232 and provides a secure mounting base for connectors 268 and anterior bracket portion 266, providing a reliable connecting means to minimize the failure of the connectors 268 and bracket portion 266 during extensive and repeated stress and strain of the anterior slope 232 and the tensioning means 250 imposed by heavily weighted users and/or highly active users of the foot support platform 200.

As illustrated in FIG. 8*a*, the alternative means for tensioning 250 includes a generally rigid posterior member 272 such as a rod or cable connected to a posterior end of a means for adjusting 270 that is adjustable by a user to length or shorten the extended end of the member 272. A posterior connector 274 is connected through a slotted connection within a posterior joint member 278 to a posterior end of the member 272, to allow pivoting 276 in an up and down, generally vertical, direction of the adjusting end of the member 272. The posterior joint member 278 includes a posterior slot 280 into which a second end 284 of a connector bracket 286 is insertable. The posterior slot 280 of joint member 278 is attachable into which a first end of bracket portion 284 to allow for lateral motion 282 (see FIG. 7) of the posterior end of joint member 278. Bracket portion 284 is integral with posterior bracket portion 286 which is connected with connectors 288 such as rivets or screws to the posterior slope base 240. The bracket portion 284 and posterior bracket portion 286 may include an angle therebetween to provide the necessary alignment with posterior slot 280 and the underside posterior slope portion 216 of the posterior slope base 240. The thick posterior slope base 240 provides rigidity for the posterior slope 238 and provides a secure mounting base for connectors 288 and posterior bracket portion 286, providing a reliable connecting means to minimize the failure of the connectors 288 and bracket portion 286 during extensive and repeated stress and strain of the posterior slope 238 and the tensioning means 250 imposed by heavily weighted users and/or highly active users of the foot support platform 210.

The means for tensioning 250 provides at least four pivotable and swiveling connector junctions along with the ability of the means for adjusting 270 to provide an extendable and retractable means for adjusting the length between connector brackets 266, 286. The means for adjusting 270 for adjusting the length between the ends of the anterior member 252 and posterior member 272 includes adjusting devices such, as a sleeve nut, worm gear, or a small-sized turnbuckle (not shown). Rotation 290 of the means for adjusting 270 may be accomplished by finger manipulation tool or with a small wrench. When rotated 290 in one direction, the anterior member 252 and posterior member 272 are retracted in overall length between the member ends, thereby pulling each respective anterior bracket 266 and posterior bracket 286 toward the means for adjusting 270. As tension is placed on each respective anterior bracket 266 and posterior bracket 286 by the retracted anterior member 252 and posterior member 272, tho brackets 266, 286 draw each respective connected portion of the anterior slope base 234 and posterior slope base 240 together, thereby inducing additional tension along the arch curve 250, forming a more rigid arch curve 250, and slightly increasing the height of the arch curve 250. When the length between anterior member 252 and posterior member 272 is extended, by rotation 290 (see FIG. 6) in an appropriate direction of the means for adjusting 270, the tension along the arch curve 230 is decreased, providing less rigid support of a user's arch at a slight decrease in the height of the arch curve 230 to a neutral height, while retaining a neutral tension along the arch curve 230. User adjustment of the means of adjusting 270 may be incremental as the user strengthens his or her arches with use of the foot support platform 210. In addition, the user can adjust the rigidity of the arch curve 230 for comfort during various walking or runing activities, and can adjust the rigidity of the arch curve 230 of either foot support platform 210 to properly support the slight variation in arch curvature between each foot.

From the foregoing description, it will be recognized by those skilled in the art that advantages of the present invention include rigidity through the arch curve portion of the adjustable arch support orthosis 100, 110, 200,210, with a flexible crown portion 132, 236, while provided a variably tensioned arch curve 130, 130', 230 to support various configurations of users' arches and feet. It is emphasized that the neutral tension along each embodiment of the continuous and non-segmented arch curve 130, 130', 230 disclosed herein, is maintainable during constant use and repetitive stress and strain, while providing a generally rigid tensioned arch curve for support of the feet of each user that is heavily weighted, and/or has medium or high arched feet. User's having arched feet or "flat feet" may benefit from use of the Therefore, users can manipulate the means for adjusting and the means for rotation to lengthen and shorten the tensioning means, to provide the user with a neutral and supportive tension along each respective arch curve 130, 130', 230, and to provide the user with an increased tension along the arch curve for increased rigidity and increased support height of each respective arch curve 130, 130', 230. During testing with a significant number of users having high and medium arches, who are also heavily weighted and provide significantly high forces on their heavily weighted arches, results are obtained that demonstrate that heavily weighted users tend to break-down the materials of prior orthotics that lack the tensioning means of the adjustable arch support orthosis disclosed herein. After repetitive use of prior orthotics by heavily weighted users, the arch curvature is reduced in height and in flex, therefore prior orthotics were reduced rapidly to non-supportive shapes by heavily weighted users. The adjustable arch support orthoses 100, 110, 200, 210 disclosed herein provides a plurality of configurations and means for tensioning for maintenance of the preferred tension and arch curve shape to consistently and repetitively support the low, medium or high arches of users, whether of average size or who are heavily weighted. With generally rigid, repetitive support of a user's arches, numerous foot disorders are avoided including plantar fasciitis and related inflamation of the connecting tissues of the feet. In addition, the adjustable arch support orthoses disclosed herein provide a method for therapeutic treatment of plantar fasciitis and related foot disorders due to the maintenance of a preferred angle of declination and a preferred tension along each arch curve 130, 130', 230, during extended use of the adjustable arch support orthoses 100, 110, 200, 210.

An alternative embodiment of the means for tensioning includes a plurality of swivel joints positioned along the respective anterior and posterior cables or bars (not shown) to allow rotation of portions of the means for tensioning during rotating of the means for adjusting. An additional embodiment of the means for tensioning includes two straps of non-extendable web material with each of the two straps having a distal end attached to the respective anterior bracket and posterior bracket connected underneath respective anterior slope and posterior slope of the arch curve (not shown). Each of the two straps have a proximal end connectable together by a means for adjusting such as a sliding buckle or a pressure clamp that is positioned under the medial longitudinal arch curve. A further additional embodiment of the means for tensioning includes a foam enclosure for either or both ends of the means for tensioning for shock absorption to reduce failure of the anterior and posterior connectors and brackets attached under the anterior and posterior portions of the adjustable arch curve. An alternative embodiment of the means for adjusting includes an anterior means for adjusting connected proximal to the anterior bracket, and a posterior means for adjusting connected proximal to the posterior bracket, with at least one cable or rod connected therebetween.

While the present invention is illustrated by description of several embodiments and while the illustrative embodiments are described in considerable detail, it is not the intention of the applicants to restrict or in any way limit the scope of the appended claims to such detail. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general inventive concept.

What is claimed is:

1. An arch support orthosis having an arch curve being adjustably tensioned during use, said arch support brace being fittable proximately under a foot and being sized and shaped to be removably placed within a foot support enclosure worn by a user, comprising:

an arch support orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and an outer lateral side on opposed sides of a central longitudinal midline of said orthosis;

a forefoot portion of said first surface being arcuately shaped to be positionable underneath the metatarsal bones of the foot;

a heel portion of said first surface being arcuately shaped to be positionable underneath the calcaneus bone of the foot;

a medial longitudinal arch curve proximate said medial side of said orthosis said medial longitudinal arch curve being shared to be positionable underneath the arch of the foot, said medial longitudinal arch curve having an upper surface being curved upwardly along a crown portion, said medial side being disposed in a continuous arched curve along a length dimension of said medial side of said orthosis, said medial longitudinal arch curve including:

an anterior slope being inclined from said upper surface of said medial longitudinal arch curve toward said forefoot portion of said orthosis;

a posterior slope being inclined from said upper surface of said medial longitudinal arch curve toward said heel portion of said orthosis;

a medial slope being inclined from said upper surface of said medial longitudinal arch curve toward said lateral side of said orthosis; and a means for tensioning said medial longitudinal arch curve connectable between an underside portion of said anterior slope and an underside portion of said posterior slope, said means for tensioning having a means for adjusting manipulated by a user for adjustment of said means for tensioning between a neutral length, a decreased length, and an extended length between said anterior slope and said posterior slope, said means for tensioning including:

an anterior bracket being L-shaped, said anterior bracket having a distal portion being connected under said anterior slope proximal to said medial side, said anterior bracket having a proximal portion extended downwardly from said anterior slope;

a posterior bracket being L-shaped, said posterior bracket having a distal portion being connected under said posterior slope proximal to said medial side, said posterior bracket having a proximal portion extended downwardly from said posterior slope;

an anterior linkage aligned with said anterior bracket, said anterior linkage having a distal end pivotably connected with said proximal portion of said anterior bracket, said anterior linkage having a proximal end disposed underneath said crown portion of said medial longitudinal arch curve;

a posterior linkage aligned with said posterior bracket, said posterior linkage having a distal end pivotably connected with said proximal portion of said posterior bracket, said posterior linkage having a proximal end disposed underneath said crown portion of said medial longitudinal arch curve; and said means for adjusting the neutral length between said distal end of said anterior linkage and said distal end of said posterior linkage, said means for adjusting having opposed ends being disposed to accept therein respectively said proximal ends of said anterior linkage and said proximal linkage, said means for adjusting being manipulated by the user;

whereby said anterior linkage and said posterior linkage are retracted into respective opposed ends of said means for adjusting by manipulation of said means for adjusting, the neutral length between said respective distal ends is shortened to said decreased length, said anterior and posterior linkages engage respective proximal portions of said anterior bracket and said posterior bracket, thereby each respective anterior and posterior brackets pivot inwardly, thereby pulling said underside of said anterior slope and said posterior slope toward each other and increasing the tension along said medial longitudinal arch curve, with resulting increase in the stiffness of said arch curve from when said means for tensioning is at the neutral length;

whereby when each of said anterior linkage and said posterior linkage is extended from said means for adjusting by manipulation of said means for adjusting, the neutral length between said respective distal ends is lengthened to said extended length, thereby each distal end extends against said respective proximal portions of said anterior bracket and said posterior bracket which pivot against the underside of said anterior slope and said posterior slope, thereby pushing said underside of said anterior slope and said posterior slope apart and reducing the tension of said medial longitudinal arch curve with resulting decrease in the stiffness of said arch curve.

2. The arch support orthosis of claim 1 wherein said means for adjusting being repeatably manipulated by the user for repetitive extension and retraction of said anterior linkage and said posterior linkage.

3. The arch support orthosis of claim 1 wherein said means for adjusting including a rotatable adjusting means having a sleeve nut, a worm gear, or a turnbuckle.

4. A foot support orthosis including an arch support brace having an arch curve being variably tensioned during use, the foot support orthosis being fittable underneath the foot and being sized and shaped to be removably placed proximal a foot supporting surface of a foot enclosure worn by a user, comprising:

an orthosis being sized for support of the foot from underneath about the metatarsal bones of the foot, to underneath about the calcaneus bone of the foot, said orthosis having a first surface being contoured for support of the foot, having a second surface being downwardly faced for contact with the foot supporting surface of the shoe, and having a medial side and a lateral side on opposed sides of a central longitudinal midline of said orthosis;

a forefoot portion of said first surface being arcuately shaped to be positionable underneath the metatarsal bones of the foot;

a heel portion of said first surface being arcuately shaped to be positionable underneath the calcaneus bone of the foot;

a medial longitudinal arch curve proximate said medial side of said orthosis, said medial longitudinal arch curve being shaped to be positionable underneath the arch of the foot, said medial longitudinal arch curve having an upper surface being curved upwardly along a crown portion, said medial longitudinal arch curve including:

an anterior slope being inclined from said upper surface of said medial longitudinal arch curve toward said forefoot portion of said orthosis;

a posterior slope being inclined from said upper surface of said medial longitudinal arch curve toward said heel portion of said orthosis; and a medial slope being inclined from said upper surface of said medial longitudinal arch curve toward said lateral side of said orthosis; and said anterior slope having an anterior base of a first thickness, said posterior slope having a posterior base of a second thickness, said crown of said medial slope having a third thickness along said upper surface of said medial longitudinal arch curve, said medial side of said medial longitudinal arch curve being disposed in a continuous arched curve along a length dimension of said medial side;

means for tensioning said medial longitudinal arch curve, said means for tensioning connectable between an underside portion of said anterior slope and an underside portion of said posterior slope, said means for tensioning having means for adjusting manipulated by the user for adjustment of said means for tensioning between a neutral length, a decreased length, and an extended length between said anterior slope and said posterior slope, said means for tensioning including:

an anterior bracket being L-shaped, said anterior bracket having a distal portion being connected under said anterior slope proximal to said medial side, said anterior bracket having a proximal portion extended downwardly from said anterior slope;

a posterior bracket being L-shaped, said posterior bracket having a distal portion being connected under said posterior slope proximal to said medial side, said posterior bracket having a proximal portion extended downwardly from said posterior slope;

an anterior linkage aligned with said anterior bracket, said anterior linkage having a distal end pivotably connected with said proximal portion of said anterior bracket, said anterior linkage having a proximal end disposed underneath said crown portion of said medial longitudinal arch curve;

a posterior linkage aligned with said posterior bracket, said posterior linkage having a distal end pivotably connected with said proximal portion of said posterior bracket, said posterior linkage having a proximal end disposed underneath said crown portion of said medial longitudinal arch curve; and said means for adjusting the neutral length between said distal end of said anterior linkage and said distal end of said posterior linkage, said means for adjusting having opposed ends being disposed to accept therein respectively said proximal ends of said anterior linkage and said proximal linkage, said means for adjusting being manipulated by the user;

whereby said anterior linkage and said posterior linkage are retracted into respective opposed ends of said means for adjusting by manipulation thereof, the neutral length between said respective distal ends is shortened to said decreased length, said anterior and posterior linkages engage respective proximal portions of said anterior bracket and said posterior bracket, thereby respective anterior and posterior brackets pivot inwardly, thereby pulling said underside of said anterior slope and said posterior slope toward each other and increasing the tension along said medial longitudinal arch curve;

whereby when each of said anterior linkage and said posterior linkage is extended from said means for tensioning by manipulation of said means for adjusting, the neutral length between said respective distal ends is lengthened to said extended length, thereby each distal end extends against said respective proximal portions of said anterior bracket and said posterior bracket which pivot against the underside of said anterior slope and said posterior slope, thereby pushing said underside of said anterior slope and said posterior slope apart and reducing the tension of said medial longitudinal arch curve, with resulting decrease in the stiffness of said arch curve for reduced support of the arch of the user's foot;

whereby said medial longitudinal arch curve being tensioned by prior manipulation of said means for adjusting by the user, said arch curve is further tensioned intermittently during each foot-strike by force being transferred by the user's foot from said heel portion and on to said medial longitudinal arch curve of said orthosis, thereby the tension along said medial longitudinal arch curve is intermittently increased without significantly decreasing the height of the arch curve thereby supporting the arch of the user's foot while said crown portion of said medial longitudinal arch curve flexibly rebounds to an unweighted position by force being transferred by the user's foot from said medial longitudinal arch curve and on to said forefoot portion of said orthosis during each foot-strike by the user wearing said orthosis.

* * * * *